United States Patent [19]

Tsuneki et al.

[11] Patent Number: 4,977,118
[45] Date of Patent: Dec. 11, 1990

[54] METHOD FOR REGENERATION OF CATALYST FOR PRODUCING OF AZIRIDINE COMPOUNDS

[75] Inventors: Hideaki Tsuneki, Tokyo; Kimio Ariyoshi; Atusi Moriya, both of Suita; Michio Ueshima, Takarazuka, all of Japan

[73] Assignee: Nippon Shokubai Kagaku Kogyo Co., Ltd., Osaka, Japan

[21] Appl. No.: 485,542

[22] Filed: Feb. 27, 1990

[30] Foreign Application Priority Data

Feb. 27, 1989 [JP] Japan ................................. 64-43331

[51] Int. Cl.$^5$ ...................... B01J 27/28; B01J 38/42; B01J 38/04; C07D 203/04
[52] U.S. Cl. ..................................... 502/35; 502/34; 548/969
[58] Field of Search ................ 502/35, 36, 34; 548/969

[56] References Cited

U.S. PATENT DOCUMENTS

| | | | |
|---|---|---|---|
| 3,474,041 | 10/1969 | Kerr | 252/411 |
| 4,774,218 | 9/1988 | Shimasaki et al. | 502/202 |
| 4,833,248 | 5/1989 | Shimasaki et al. | 548/969 |
| 4,841,060 | 6/1989 | Hino et al. | 502/202 |
| 4,841,061 | 6/1989 | Shimasaki et al. | 502/202 |
| 4,861,738 | 8/1989 | Edwards | 502/35 |

FOREIGN PATENT DOCUMENTS 0228898 12/1986 European Pat. Off. .
0263005 9/1987 European Pat. Off. .
0284872 3/1988 European Pat. Off. .
2209478 3/1988 United Kingdom .

*Primary Examiner*—Paul E. Konopka
*Attorney, Agent, or Firm*—Sherman and Shalloway

[57] ABSTRACT

A method for regeneration of catalyst which comprises phosphorus and alkali metal element and/or alkaline earth metal element and was deteriorated by use to produce aziridine compound represented by the general formula

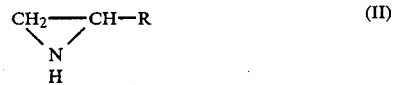 (II)

wherein R is hydrogen, a methyl group or an ethyl group, by a catalytic vapor-phase intramolecular dehydration reaction of alkanolamine represented by the general formula

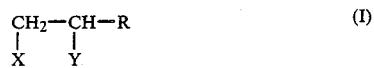 (I)

wherein R is as defined in the formula (II), X is OH or $NH_2$, and Y is either $NH_2$ when X is OH or OH when X is $NH_2$, characterized in that the deteriorated catalyst is contacted with gaseous volatile phosphorus compound.

9 Claims, No Drawings

METHOD FOR REGENERATION OF CATALYST FOR PRODUCING OF AZIRIDINE COMPOUNDS

This invention relates to a method for regeneration of catalyst. More specifically, the invention relates to a method for regeneration of catalyst to be used in production of aziridine compound represented by the general formula

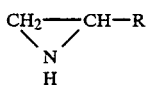

by a vapor-phase intramolecular dehydration reaction of alkanolamine represented by the general formula

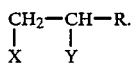

In the above formula, R represents hydrogen, a methyl group or an ethyl group, X represents OH or $NH_2$, and Y represents either $NH_2$ when X is OH or OH when X is $NH_2$.

The aziridine is a cyclic compound having a 3-membered ring with a large distortion. It has both ring-opening reactivity and the reactivity of an amine, and is useful as an intermediate for various compounds. In particular, ethylenimine has already gained widespread acceptance in the industry as a material for agricultural chemicals and pharmaceuticals and for amine-type polymers which are useful as textile treating agents. The present invention provides a method to regeneration of excellent catalyst capable of effectively producing aziridine compounds having a higher utilizable value when it is deactivated by a long-term reaction.

A generally well-known method of producing an aziridine compound is typically a method of producing ethylenimine which comprises treating monoethanolamine sulfate in the liquid phase with a concentrated alkali solution, which has already been industrially practiced. This method, however, has many defects in industrial practice. For example, because of the need for using large amounts of sulfuric acid and an alkali as subsidiary materials, it has low productivity. Moreover, inorganic salts of low utilitarian value are formed as by-products.

In an attempt to remove the defects of aziridine production by such a liquid-phase method, various methods have been reported recently for the direct production of an aziridine compound by intramolecular dehydration reaction of an alkanolamine in the vapor phase in the presence of a catalyst without using subsidiary materials directly, and it has been reported that catalyst containing phosphorus exhibits particularly excellent performances (EP-A No. 228,898 and EP-A No. 230,776).

However, as a result of further investigation by the present inventors, it has been revealed that the above method wherein alkanolamine is subjected to the vapor-phase intramolecular dehydration reaction in the presence of catalyst containing phosphorus has drawbacks that even when catalyst having a comparatively long catalyst life is used, deposit of carbonaceous substances is recognized, its catalytic activity gradually deteriorates or pressure loss of the catalyst layer increases, and finally continuation of the reaction becomes difficult. It is possible to temporarily solve this problem by contacting the catalyst with an oxygen-containing gas to burn and remove the cokes. However, in a long-term reaction over a period of 5,000 to 10,000 hours, even if combustion and removal of the cokes are repeated, gradual lowering of its catalytic activity cannot be avoided. As in industrial use of the catalyst it is necessitated that the catalyst exhibit a stable activity over a long period, it is a large problem that such deterioration is recognized.

As a result of extensive investigation on cause of this deactivation and its solution method, the present inventors have found that activity deterioration arises mainly by scattering of phosphorus in the catalyst components during the reaction. They further vigorously investigated various methods to recover its activity, and as a result found that the catalyst can be regenerated by supplying phosphorus lost during the reaction thereto. Specifically, it is possible to supply the deteriorated catalyst with phosphorus by contacting the catalyst with gaseous volatile phosphorus compound (phosphoric ester, phosphorus ester, phosphorus pentoxide, phosphorus halide, phosphoryl halide or the like), and thereby the catalyst can easily and promptly be regenerated.

Thus, according to the present invention there is provided a method for regeneration of catalyst which comprises phosphorus and alkali metal element and/or alkaline earth metal element and was deteriorated by use to produce aziridine compound represented by the general formula

wherein R is hydrogen, a methyl group or an ethyl group, by a catalytic vapor-phase intramolecular dehydration reaction of alkanolamine represented by the general formula

wherein R is as defined in the formula (II), X is OH or $NH_2$, and Y is either $NH_2$ when X is OH or OH when X is $NH_2$, characterized in that the deteriorated catalyst is contacted with gaseous volatile phosphorus compound.

As the catalyst which is used in the vapor-phase intramolecular dehydration reaction of alkanolamine in the invention and comprises phosphorus, alkali metal element and/or alkaline earth metal element, is preferred a composition represented by the general formula

wherein P represents phosphorus, A represents at least one element selected from alkali metal elements and alkaline earth metal elements, B represents at least one element selected from elements of group IIIa, Si, Ge, Sn, Pb, Sb, Bi, transition metal elements of group I to VIII, lanthanide elements and actinide elements in the periodic table, and O represents oxygen, and the suffixes a, b, c and d represent number of element and when a is 1, b is 0.01 to 6, preferably 0.1 to 3 and c is 0 to 6, preferably 0.001 to 5, and d is a value determined by a, b and c and the state of bonding of the constituent elements,
because the composition exhibits particularly excellent performances. Such catalyst may be used as supported on various carriers such as silica, alumina, silicon carbide, diatomaceous earth, zirconia and clay mineral.

Any phosphorus compound can be used as the phosphorus compound to be used for regeneration of the catalyst in the invention so long as it is volatile. However, those having a boiling point of 300° C. or less in case of liquid and those having a sublimation pressure at 300° C. of 100 mmHg or more in case of solid are preferred from the aspects of apparatus and procedure because it becomes possible to supply the phosphorus compound in a sufficient concentration without necessity of particularly high temperature. Examples of such volatile phosphorus compounds include organic phosphorus compounds such a phosphoric esters and phosphorus esters and inorganic phosphorus compounds such as phosphorus pentoxide, phosphorus halides and phosphoryl halides. Among them, phosphoric acid alkyl esters such as trimethyl phosphate and triethyl phosphate and phosphorus acid alkyl esters such as trimethyl phosphite and triethyl phosphite have a low boiling point, have no corrosivity and are liquid at normal temperatures, and hence, are convenient in handling.

If the quantity of the volatile phosphorus compound to be contacted with the deteriorated catalyst is too small, sufficient catalytic activity cannot be regenerated, and too much quantity thereof is of no use. Preferred quantity thereof is the order corresponding to 0.8 to 1.2 times the molar quantity of the phosphorus lost from the catalyst by the catalytic vapor-phase intramolecular dehydration reaction. Quantity of the lost phosphorus can be estimated by analysis of the deteriorated catalyst or analysis of the phosphorus contained in the products produced by the catalytic vapor-phase intramolecular dehydration reaction.

It is adequate that the temperature at which the deteriorated catalyst is contacted with the volatile phosphorus compound is temperature at which the phosphorus compound has a sufficient vapor pressure and can maintain a gaseous state. If the temperature is too low, quantity of the phosphorus compound which volatilizes is small and it takes a long time for the regeneration treatment, whereas if the temperature is made to be high beyond the necessity, new equipments therefor becomes necessary. Preferred temperatures are those between temperature higher by 100° C. than the temperature of the catalytic vapor-phase intramolecular dehydration reaction of the alkanolamine and temperature lower by 100° C. than the temperature of the reaction.

If the concentration of the volatile phosphorus compound in the regeneration procedure is too low, quantity of the phosphorus compound which volatilizes is small and it takes a long time for the regeneration treatment, whereas if the concentration becomes too high, the catalyst becomes hard to uniformly regenerate or a high temperature becomes necessary to maintain a sufficient vapor pressure. Thus, it is preferred that the concentration is in the range of 0.01 to 5% by volume.

Since in the present reaction after comparatively short time lapse (100 to 300 hours) carbonaceous substances deposit on the catalyst and it becomes impossible to continue the reaction, usually the reaction is then stopped and the carbonaceous substances are removed by combustion with an oxygen-containing gas. The catalyst-regenerating treatment in the invention can be made successively after the procedure of removal of the carbonaceous substances by combustion. By thus making the phosphorus compound treatment successively every after the removal procedures of the carbonaceous substances by combustion, it is possible to substantially prevent deterioration of activity of the catalyst.

When the deteriorated catalyst is contacted with gaseous volatile phosphorus compound, it is also possible to carry out the treatment after the catalyst was once taken out from the reactor, but it is convenient to carry out the treatment in situ, i.e. with the catalyst packed as it is in the reactor. It is also possible that plural reactors are installed and while some reactor(s) is regenerated the reaction is carried out in the other reactor(s) to carry out substantially continuous operation.

Although not perfectly revealed, the function of the invention is roughly surmised as follows. It is recognized that in the deactivated catalyst phosphorus, which is a catalyst component, is clearly decreased compared to the catalyst before the reaction. Thus, it is surmised that on the surface of the catalyst, metals which were present as phosphate before deactivation is present as oxide or hydroxide. When gaseous phosphorus compound is reacted therewith, metal phosphate similar to that before the deactivation is regenerated on the surface and catalytic activity restores.

The present invention is described in more detail below according to Examples.

Conversion, selectivity and one-pass yield in the examples are defined as follows:

Conversion (mole %) =

$$\frac{\text{moles number of alkanolamine consumed}}{\text{moles number of alkanolamine supplied}} \times 100$$

Selectivity (mole %) =

$$\frac{\text{moles number of aziridine compound formed}}{\text{moles number of alkanolamine consumed}} \times 100$$

One-pass yield (mole %) =

$$\frac{\text{moles number of aziridine compound formed}}{\text{moles number of alkanolamine supplied}} \times 100$$

EXAMPLE 1

Preparation of catalyst

Calcium hydroxide (74.1 g) and 4.0 g of sodium hydroxide were suspended in 200 ml of pure water, and 57.6 g of 85% by weight orthophosphoric acid was added. The mixture was concentrated with heating while stirring adequately and evaporated to dryness on a water bath. The dried matter was then dried in the air at 120° C. for 12 hours and pulverized, 20 g of 0.01% by weight aqueous palladium nitrate solution was added, and the mixture was sufficiently kneaded. The kneaded matter was dried in the air at 120° C. for 12 hours, fractured to 9 to 5 mesh and calcined at 700° C. for 5 hours to obtain a catalyst having the composition of $P_1Ca_2Na_{0.2}$ (Pd 10 ppm) in terms of atomic ratio.

Reaction step

Synthesis of 2-methylethyleneimine by a catalytic vapor-phase intramolecular dehydration reaction of monoisopropanolamine was carried out using this catalyst as follows.

This catalyst (20 ml) was packed in a stainless reaction tube having an inner diameter of 16 mm, and the reaction tube was immersed in a molten salt bath of 420° C. A raw material gas consisting of 10% by volume of monoisopropanolamine and 90% by volume of nitrogen was passed through the reaction tube at a space velocity of 3,000 hr$^{-1}$ to carry out a reaction for 200 hours.

Then, air was passed through the reaction tube at the same temperature as that during the reaction for 24 hours, and the carbonaceous substances deposited on the surface of the catalyst during the reaction were burned.

Cycle of this reaction-combustion was repeated 40 times to carry out the reaction for 8,000 hours in total, whereby performances of the catalyst were lowered by 13.8% in terms of conversion after the 8,000 hours reaction, compared to early stage of start of the use.

Regeneration step

A gas consisting of 2% by volume trimethyl phosphate and 98% by volume nitrogen was passed through this catalyst at a flow rate of 100 ml per minute at 380° C. for 30 minutes to carry out regeneration treatment of the catalyst.

Catalyst test

Reaction was carried out in the same manner as described in the above "reaction step" using the catalyst after the regeneration treatment, and 2 hours after the start of the reaction, conversion, selectivity and one-pass yield were measured.

Reaction results at an early stage of the reaction, after the 8,000 hour reaction and after the regeneration treatment were indicated in Table-1.

EXAMPLE 2

Preparation of catalyst (A)

Cesium nitrate (1.754 kg), 40 g of sodium hydroxide and 922 g of 85% by weight of phosphoric acid were dissolved in 30 l by pure water, 6 kg of silica gel was added as a carrier, and further 38 g of aluminum nitrate was added. The mixture was concentrated with heating and evaporated to dryness in a water bath. The resulting dried matter was dried at 120° C. for 12 hours and pulverized. Then, 1.95 kg of 0.001% by weight aqueous chloroplatinic acid solution and an appropriate quantity of deionized water were added, followed by sufficient kneading. The kneaded matter was molded into rings having an outer diameter of 6 mm, an inner diameter of 2 mm and a length of 8 mm, dried at 120° C. for 12 hours, and calcined at 700° C. for 4 hours to give a catalyst (A) having the composition of $P_1Cs_{1.125}Na_{0.125}Al_{0.0125}$ (Pt 1 ppm) in terms of atomic ratio.

Reaction step

Synthesis of ethyleneimine by catalytic vapor-phase intramolecular dehydration reaction of monoethanolamine was carried out using this catalyst (A) as follows.

This catalyst (A)(2 l) was packed in a stainless reaction tube having an inner diameter of 30 mm, and the resulting reaction tube was immersed in a molten salt bath of 390° C. While pressure at the outlet of the reaction tube is maintained at a reduced pressure of 80 mmHg, monoethanolamine was passed therethrough at a space velocity of 300 hr$^{-1}$ to carry out a reaction for 200 hours.

Then, air was passed through the reaction tube at the same temperature as that during the reaction for 24 hours to burn the carbonaceous substances deposited in the reaction.

Cycle of this reaction-combustion was repeated 40 times to carry out the reaction for 8,000 hours in total.

Preparation of catalyst (B)

The resulting catalyst (A) after the reaction for 8,000 hours in total was taken out from the reaction tube and pulverized to 9 to 16 mesh to prepare a catalyst (B).

Catalyst test

The catalyst (B)(20 ml) was packed in a stainless reaction tube having an inner diameter of 16 mm, and the reaction tube was immersed in a molten salt bath of 390° C. While outlet pressure of the reaction tube was maintained at a reduced pressure of 80 mmHg, monoethanolamine was passed through the tube at a space velocity of 300 hr$^{-1}$ to carry out a reaction. Two hours after start of the reaction conversion, selectivity and one-pass yield were measured.

Separately, in order to measure performances of the catalyst of the present example in the early stage of the reaction, catalyst test was carried out similarly using the unused catalyst (A) fractured to 9 to 16 mesh.

Activity of the catalyst (B) was lowered by 10.3% compared to the catalyst at early stage of the reaction.

Regeneration step

A gas consisting of 2% by volume of trimethyl phosphate and 98% by volume of nitrogen was passed through this deteriorated catalyst (B) at a flow rate of 100 ml per minute at the same temperature as that during the reaction to carry out a regeneration treatment for 30 minutes.

Catalyst test

Catalyst test was conducted in the same manner as above using the catalyst after the regeneration treatment.

Reaction results at early stage of the reaction, after the 8,000 hour reaction and after the regeneration treatment were indicated in Table-1 together with the results of the above catalyst test.

In the following examples 3 to 6, regeneration step and catalyst test were carried out using the deteriorated catalyst (B) after it had been used in the reaction for 8,000 hours in total. Therefore, the results at the early stage of the reaction and after the 8,000 hour reaction in Examples 3 to 6 are the same as in Example 2.

EXAMPLE 3

Regeneration step

The catalyst (B) was packed into the reactor in the same manner as in Example 2, and a gas consisting of 1% by volume of triethyl phosphate and 99% by volume of nitrogen was passed through the reactor at a flow rate of 200 ml per minute at the same temperature as the reaction temperature to carry out a regeneration treatment for 40 minutes.

Catalyst test

Catalyst test was conducted in the same manner as in Example 2 using the catalyst after the regeneration treatment.

Reaction result after the regeneration treatment was shown in Table-1.

EXAMPLE 4

Regeneration step

The catalyst (B) was packed into the reactor in the same manner as in Example 2, and a gas consisting of 2% by volume of triethyl phosphite and 98% by volume of nitrogen was passed through the reactor at a flow rate of 100 ml per minute at the same temperature as the reaction temperature to carry out a regeneration treatment for 40 minutes.

Catalyst test

Catalyst test was carried out in the same manner as in Example 2 using the catalyst after the regeneration treatment.

Reaction result after the regeneration treatment was indicated in Table-1.

EXAMPLE 5

Regeneration step

The catalyst (B) was packed into the reactor in the same manner as in Example 2, and a gas consisting of 3% by volume of phosphoryl chloride and 97% by volume of nitrogen was passed through the reactor at a flow rate of 100 ml per minute at the same temperature as the reaction temperature to carry out a regeneration treatment for 30 minutes, and then air was flowed therethrough at a flow rate of 100 ml per minute for further 30 minutes.

Catalyst test

Catalyst test was carried out in the same manner as in Example 2 using the catalyst after the regeneration treatment.

Reaction result after the regeneration treatment was indicated in Table-1.

EXAMPLE 6

Regeneration step

The catalyst (B) was packed into the reactor in the same manner as in Example 2. Phosphorus pentoxide (180 mg) was built up at the inlet- of the catalyst layer, and air was passed through the reactor at a flow rate of 100 ml per minute at 300° C. to carry out a regeneration treatment for 30 hours.

Catalyst test

Catalyst test was carried out in the same manner as in Example 2 using the catalyst after the regeneration treatment.

EXAMPLE 7

The catalyst (A) in Example 2 was fractured into 9 to 5 mesh size. The fractured catalyst (20 ml) was packed into a stainless reaction tube having an inner diameter of 16 mm, and the reaction tube was immersed in a molten salt bath of 390° C. While the outlet pressure was maintained at a reduced pressure of 80 mmHg, monoethanolamine was passed through the reaction tube at a space velocity of 300 hr$^{-1}$ to carry out reaction for 200 hours.

Then, air was passed therethrough at the same temperature as at the reaction time for 23 hours to burn the carbonaceous substances deposited on the surface of the catalyst in the reaction. Thereafter, a gas consisting of 0.2% by volume of trimethyl phosphate and 99.8% by volume of nitrogen was passed through the reaction tube for 10 minutes to make a regeneration treatment.

This cycle of reaction-combustion-regeneration was repeated 40 times to carry out reaction for 8,000 hours in total.

Reaction results at the early stage of the reaction, after the 8,000 hour-reaction and after the regeneration treatment were indicated in Table-1.

By conducting regeneration by phosphorus compound after combustion and removal of the carbonaceous substances, lowering of activity was scarcely observed.

EXAMPLE 8

Preparation of catalyst

Aluminium nitrate nonahydrate (112.5 g) was dissolved in 300 ml of pure water, and a solution of 44.7 g of triammonium phosphate in 300 ml of pure water was added thereto with stirring. The resulting precipitate was collected by filtration, and washed with water. A solution of 2.25 g of cesium hydroxide in 10 ml of water was added thereto, and the mixture was sufficiently kneaded and dried at 120° C. for 12 hours. The resultant solid matter was fractured into 16 to 9 mesh size and calcined at 1,000° C. for 2 hours to obtain a catalyst having the composition of $P_1Cs_{0.05}Al_1$ in terms of atomic ratio.

Reaction step

This catalyst (5 ml) was packed into a stainless reaction tube having an inner diameter of 10 mm and the reaction tube was immersed in a molten salt bath of 430° C. A raw material gas consisting of 5% by volume of monoethanolamine and 95% by volume of nitrogen was passed through the reaction tube at a space velocity of 500 hr$^{-1}$ to carry out reaction for 95 hours.

Then, air was passed through the reaction tube at the same temperature as at the reaction time for 4 hours to burn the carbonaceous substances deposited during the reaction.

This cycle of reaction-combustion was repeated 20 times to carry out reaction for 1,900 hours in total.

Activity lowering of 8.1% in terms of conversion was observed 1,900 hours after start of the reaction, compared to the early stage of start of the reaction.

Regeneration step

A gas consisting of 1% by volume of triethyl phosphate and 99% by volume of nitrogen was flowed through the catalyst after use in this 1,900 hour-reaction at a flow rate of 100 ml per minute at 430° C. to make a regeneration treatment for 30 minutes.

Catalyst test

The same catalyst test as above was carried out using the catalyst after the regeneration treatment.

Reaction results at the early stage of the reaction, after the 1,900 hour-reaction and after the regeneration treatment were indicated in Table-1.

EXAMPLE 9

Reaction of 1,900 hours in total was carried out in the same manner as in Example 8 except that Example 8 was altered so that successively after each of 20 time-combustion-removal treatments of the carbonaceous substances, a gas consisting of 0.15% by volume of triethyl phosphate and 99.85% by volume of nitrogen was passed therethrough at a flow rate of 100 ml per minute at the same temperature as at the time of the reaction to make a regeneration treatment for 10 minutes. Reaction results at the early stage of the reaction, after the 1,900 hour-reaction and after the regeneration treatment were indicated in Table-1.

TABLE 1

| Example | Catalyst composition | Volatile phosphorus compound | Raw material alkanolamine (I) | Produced aziridine compound (II) | SV (hr-1) | Reaction temperature (°C.) | Raw material concentration % | Reaction lapse time (hr) | (I) Conversion (mole %) | (II) Selectivity (mole %) | (II) One-pass (mole %) |
|---|---|---|---|---|---|---|---|---|---|---|---|
| 1 | P$_1$Ca$_2$Na$_{0.2}$ | Trimethyl phosphate | Monoisopropanolamine | 2-methyl-ethyleneimine | 3,000 | 420 | 10 | 2 | 50.7 | 79.9 | 40.5 |
|  |  |  |  |  |  |  |  | 8,000 | 36.9 | 78.0 | 28.8 |
|  |  |  |  |  |  |  |  | after regeneration 2 | 49.9 | 80.3 | 40.1 |
| 2 | P$_1$Cs$_{1.125}$Na$_{0.125}$Al$_{0.0125}$ | Trimethyl phosphate | Monoethanolamine | Ethyleneimine | 300 | 390 | 100 | 2 | 39.8 | 86.6 | 34.5 |
|  |  |  |  |  |  |  |  | 8,000 | 29.5 | 85.3 | 25.2 |
|  |  |  |  |  |  |  |  | after regeneration 2 | 39.2 | 86.8 | 34.0 |
| 3 | P$_1$Cs$_{1.125}$Na$_{0.125}$Al$_{0.0125}$ | Trimethyl phosphate | Monoethanolamine | Ethyleneimine | 300 | 390 | 100 | after regeneration 2 | 40.5 | 83.9 | 34.0 |
| 4 | P$_1$Cs$_{1.125}$Na$_{0.125}$Al$_{0.0125}$ | Triethyl phosphite | Monoethanolamine | Ethyleneimine | 300 | 390 | 100 | after regeneration 2 | 38.9 | 86.9 | 33.8 |
| 5 | P$_1$Cs$_{1.125}$Na$_{0.125}$Al$_{0.0125}$ | Phosphoryl chloride | Monoethanolamine | Ethyleneimine | 300 | 390 | 100 | after regeneration 2 | 37.4 | 86.4 | 32.3 |
| 6 | P$_1$Cs$_{1.125}$Na$_{0.125}$Al$_{0.0125}$ | Phosphorus pentoxide | Monoethanolamine | Ethyleneimine | 300 | 390 | 100 | after regeneration 2 | 36.1 | 85.3 | 30.8 |
| 7 | P$_1$Cs$_{1.125}$Na$_{0.125}$Al$_{0.0125}$ | Trimethyl phosphate | Monoethanolamine | Ethyleneimine | 300 | 390 | 100 | 2 | 40.0 | 86.5 | 34.6 |
|  |  |  |  |  |  |  |  | with regeneration 8,000 | 39.6 | 86.4 | 34.2 |
| 8 | P$_1$Cs$_{0.05}$Al$_1$ | Triethyl phosphate | Monoethanolamine | Ethyleneimine | 1,500 | 430 | 5 | 2 | 81.3 | 80.0 | 65.0 |
|  |  |  |  |  |  |  |  | 1,900 | 73.2 | 81.2 | 59.4 |
|  |  |  |  |  |  |  |  | after regeneration 2 | 80.1 | 80.3 | 64.3 |
| 9 | P$_1$Cs$_{0.05}$Al$_1$ | Triethyl phosphate | Monoethanolamine | Ethyleneimine | 1,500 | 430 | 5 | 2 | 82.0 | 79.8 | 65.4 |
|  |  |  |  |  |  |  |  | with regeneration 1,900 | 81.4 | 80.0 | 65.1 |

We claim:

1. A method for regeneration of catalyst which comprises phosphorus and alkali metal element and/or alkaline earth metal element and was deteriorated by use to produce aziridine compound represented by the general formula

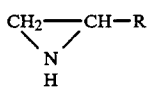  (II)

wherein R is hydrogen, a methyl group or an ethyl group, by a catalytic vapor-phase intramolecular dehydration reaction of alkanolamine represented by the general formula

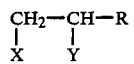  (I)

wherein R is as defined in the formula (II), X is OH or NH$_2$, and Y is either NH$_2$ when X is OH or OH when X is NH$_2$, characterized in that the deteriorated catalyst is contacted with gaseous volatile phosphorus compound.

2. The method of claim 1 wherein said volatile phosphorus compound is volatile phosphorus compound having a boiling point at 1 atmospheric pressure of 300° C. or less.

3. The method of claim 1 wherein said volatile phosphorus compound is phosphoric acid alkyl ester and/or phosphorus acid alkyl ester.

4. The method of claim 1 wherein said volatile phosphorus compound is volatile phosphorus compound having a sublimation pressure at 300° C. of 100 mmHg or more.

5. The method of claim 2 or 4 wherein said volatile phosphorus compound is at least one selected from phosphorus oxide, phosphorus halide and phosphoryl halide.

6. The method of claim 1 wherein volatile phosphorus compound of 0.8 to 1.2 times the molar quantity of the phosphorus lost from the catalyst by the catalytic vapor-phase intramolecular dehydration reaction is contacted with the deteriorated catalyst.

7. The method of claim 1 wherein said deteriorated catalyst is contacted with said volatile phosphorus compound at temperature between temperature higher by 100° C. than the temperature of the catalytic vapor-phase intramolecular dehydration reaction of the alkanolamine and temperature lower by 100° C. than the temperature of the reaction.

8. The method of claim 1 wherein the concentration of said volatile phosphorus compound is 0.01 to 5% by volume.

9. The method of claim 1 wherein said catalyst is composition represented by the general formula

wherein P represents phosphorus, A represents at least one element selected from alkali metal elements and alkaline earth metal elements, B represents at least one element selected from elements of group IIIa, Si, Ge, Sn, Pb, Sb, Bi, transition metal elements of group I to VIII, lanthanide elements and actinide elements in the periodic table, and O represents oxygen, and the suffixes a, b, c and d represent number of element and when a is 1, b is 0.01 to 6, preferably 0.1 to 3 and c is 0 to 6, preferably 0.001 to 5, and d is a value determined by a, b and c and the state of bonding of the constituent elements.

* * * * *